United States Patent [19]

Kramer et al.

[11] Patent Number: 5,292,535
[45] Date of Patent: Mar. 8, 1994

[54] HYPEROSMOTIC SOLUTIONS FOR ISONATREMIC RESUSCITATION

[75] Inventors: George C. Kramer, Davis; Azad Sheikh, Elk Grove; Robert A. Gunther, Davis, all of Calif.

[73] Assignee: Regents of the University of California, Oakland, Calif.

[21] Appl. No.: 538,848

[22] Filed: Jun. 15, 1990

[51] Int. Cl.$^5$ .................. A61K 33/14; A61K 37/00; A61K 31/70; A61K 31/195
[52] U.S. Cl. ........................... 424/680; 514/2; 514/23; 514/561; 514/921
[58] Field of Search .............. 424/680; 514/561, 2, 514/23, 921

[56] References Cited

U.S. PATENT DOCUMENTS

| | | | |
|---|---|---|---|
| 3,356,570 | 12/1967 | Butcher, Jr. | 424/680 |
| 4,025,650 | 5/1977 | Gans et al. | 424/680 |
| 4,042,687 | 8/1977 | Gans et al. | 424/680 |
| 4,042,688 | 8/1977 | Gans et al. | 424/680 |
| 4,049,795 | 9/1977 | Laborit | 424/680 |
| 4,053,589 | 10/1977 | Gans et al. | 424/680 |
| 4,308,255 | 12/1981 | Raj et al. | 514/23 |
| 4,434,160 | 2/1984 | Jeretin et al. | 424/680 |
| 4,446,154 | 5/1984 | Osterholm | 424/680 |
| 4,446,155 | 5/1984 | Osterholm | 424/680 |
| 4,604,286 | 8/1986 | Kawajiri | 424/680 |
| 4,670,261 | 6/1987 | Samejima et al. | 514/23 |
| 4,908,350 | 5/1990 | Kramer et al. | 424/680 |
| 4,981,687 | 1/1991 | Fregly et al. | 424/680 |

FOREIGN PATENT DOCUMENTS

| | | |
|---|---|---|
| 0176094 | 4/1986 | European Pat. Off. |
| 0245105 | 11/1987 | European Pat. Off. |
| 1171052 | 11/1969 | United Kingdom |

OTHER PUBLICATIONS

Modig, Biol. Abstracts, 78(3) 2473 No. 21745 (1983).
Pristoupil and Stanislav, Chem. Abstracts, vol. 82, No. 4772b (1985).
Shimazaki et al., Body Fluid Changes During Hypertonic Lactated Saline Solution Therapy for Burn Shock, J. Trauma 17:38–43 (1977).
Lopes et al., Hyperosmotic NaCl and severe hemorrhagic shock: role of the innervated lung, Am. J. Physiol. 241:H883–H8889.
Rush, B. F., Treatment of experimental shock: Comparison of the effects or norepinephrine, Dibenzyline, dextran, whole blood and balanced saline solutions, Surgery, 61:938–944 (1967).
Velasco et al., Hyperosmotic NaCl and severe hemorrhagic shock, Am. J. Physiol., 239:H664–H673 (1980).
Fraser and Cowell, Nature and Treatment of Wound Shock and Allied Conditions, Journal A.M.A., pp. 521–535, Feb. 23 (1918).
Danowski et al., The treatment of Shock Due to Salt Depletion; Comparison of the Hemodynamic Effects of Isotonic Saline, of Hypertonic Saline, and of Isotonic Glucose Solutions, J.C.I., 25:130–138 (1946).
Brooks et al., Osmolar and Electrolyte Changes in Haemorrhagic Shock The Lancet, pp. 521–527, Mar. 9, 1963.
Silbert, S., The Treatment of Thromboangiitis Obliterans, Journal A.M.A., pp. 1759–1761, Jun. 5, 1926.
Baue et al, A Comparison of Isotonic and Hypertoni Solutions on Blood on Blood Flow and Oxygen Consumption in the Initial Treatment of Hemorrhagic Shock, J. Trauma 1:743–756 (1967).

*Primary Examiner*—Frederick E. Waddell
*Assistant Examiner*—Raymond J. Henley, III
*Attorney, Agent, or Firm*—Campbell and Flores

[57] ABSTRACT

The invention provides a physiologically acceptable solution for treating circulatory shock in mammals which is hyperosmotic as compared to blood plasma. The solution contains a reabsorbable solute and sodium salt in a concentration having an osmolarity in excess of about 1000 mOsms. The physiologically acceptable solution can be easily administered by rapid infusion of 4–6 ml/kg body weight and results in rapid normalization of circulatory function.

7 Claims, No Drawings

HYPEROSMOTIC SOLUTIONS FOR ISONATREMIC RESUSCITATION

BACKGROUND OF THE INVENTION

The present invention was made with support of NIH grant number HL 40296-01. The United States Government has rights in the invention.

This invention relates generally to the area of treatments for circulatory shock and more specifically to a solution which is hyperosmotic for use in preventing and treating hypodynamic shock.

While field therapy of many medical emergencies, such as cardiac arrest, asthmatic attacks and diabetic crises has become highly successful due to the ever increasing amount of effective drugs, considerably less success has been realized with field treatment of trauma and shock. Many studies suggest that a substantial number of patients dying from traumatic injuries could have survived if the level of trauma care had been more advanced. Initial therapy of trauma and hemorrhage currently usually centers on effecting the cessation of bleeding and on the infusion of large volumes of solutions to replace lost blood volume. Large volume infusion (2 to 8 liters) has generally been considered necessary to restore normal circulatory functions such as arterial blood pressure, cardiac output, oxygen consumption and renal function. Such treatment must be accomplished rapidly to be effective. The initial treatment period can be critical in some clinical situations, especially with mass casualities as in the battlefield or large disasters.

The infusion of large volumes of solution involves risks and complications, however. Fluid overload, or "overexpansion", and congestive pulmonary atelectasis may result after use of excessive amounts of fluid. Untreated hemorrhage can be rapidly fatal. Limited personnel and difficult conditions at the site of an accident make adequate field resuscitation difficult to impossible. In addition to the time necessary merely to infuse such volumes, critical minutes are lost due to difficulties in gaining access to the vascular system. Paramedical personnel must be highly trained to perform such operations. As a result, the average trauma patient has received only 700 ml of fluid prior to arrival in the emergency room, a volume which is normally insufficient to effectively treat hypodynamic shock. Therefore, due to the large volumes of fluid required by trauma patients, field therapy is often inadequate.

Likewise, resuscitation and circulatory support are also required of many critically ill patients treated in emergency and operating rooms and intensive care units. Patients suffering from failure of vital organs such as the heart, liver or lungs, often develop circulatory shock and require volume support. An insidious and not infrequent complication of patients suffering from trauma, burns, and surgical complications is sepsis, which can lead to Adult Respiratory Distress Syndrome (ARDS) and Multi-Organ Failure (MFO). These patients require massive amounts of conventional fluids over several days to maintain adequate cardiovascular function. It has been suggested that ARDS and MFO may develop from fluid overload. Because ARDS and MFO are usually fatal, there is a critical need for more effective resuscitation regimens.

Fluid replacement infusion normally utilizes solutions which have a similar osmolarity to blood plasma. Osmolarity refers to the total concentration of molecules or solutes in a solution. Water will tend to move across a semi-permeable membrane into a solution having a higher concentration of solutes. Thus, the introduction into, for example, the blood vessels, of a fluid having an osmolarity higher than that of normal body fluids will establish an osmotic gradient across the membranes, resulting in an initial change of fluid volume within the vascular system. Osmolarity is generally expressed as millimoles per liter of solution or mOsms. Blood plasma has an osmolarity of about 283 to 295 mOsms; solutions which exceed these levels are termed hyperosmotic.

Conventional isotonic fluids are only effective when given in large volumes because only ¼ to ⅓ of standard crystalloid solutions remains in the circulation after intravenous infusion. Most of this fluid sequesters in the interstitial space. In those critically ill patients with inflammation and tissue injury, a capillary leak syndrome exists and even more infused fluid leaves the circulation. This interstitial fluid expansion or edema may cause decreased tissue oxygenation, delayed wound healing and increased rates of infection. Thus, it is evident that there exists a need for more effective resuscitation fluids. A resuscitation regimen effective at restoring and maintaining cardiovascular function in smaller volumes would limit life threatening medical complications in critically ill patients.

Recently, successful resuscitation of hemorrhaged animals and injured patients has been accomplished with highly hyperosmotic saline solutions, having an osmolarity in the range of 2400 mOsms or greater. Such treatment has the advantage of requiring smaller total fluid volume and results in brief initial promotion of circulatory function.

The primary mechanism for hypertonic saline resuscitation is mobilization and redistribution of interstitial and cellular water into the circulation. Thus, hypertonic saline infusions expand plasma and vascular volume. Several other direct and indirect physiological effects of hypertonic saline infusions probably contribute to its ability to resuscitate circulatory shock as well. These include: reduction of interstitial and cellular edema, increased cardiac contractility, peripheral vasodilation with a subsequent reduced cardiac afterload, increased mesenteric blood flow, normalization of both cellular membrane potentials and intracellular electrolyte composition. A major limitation of hypertonic saline therapy in its present form is that its effects are not stable or long-lasting. If greater concentrations of saline are infused, more benefit can be achieved, but serum sodium levels soon reach a level (>170–180 mEq/L) that may be dangerous and thus requires discontinuation of the infusion. This resulting hypernatremia may be the most severe limitation of current hypertonic resuscitation.

Hyperosmotic solutions, containing such solutes as glucose, mannitol, sodium chloride, sodium acetate, sodium bicarbonate, over a wide range of volumes and at variable osmotic strengths, have all been studied. Infusion of such solutions increase arterial pressure, cardiac output and oxygen consumption. However, it has been found that sodium salts are more effective than glucose or mannitol, probably due to excessive urine losses associated with these sugars. The reversal of shock by these hyperosmotic infusions alone is transient, as is the case for hypertonic saline. Mannitol is rapidly excreted by the kidney after infusion because there is no reabsorption by renal tubules. Glucose is somewhat better since some glucose is reabsorbed. However, after a hypertonic infusion, the tubular reabsorption carrier becomes saturated and glucose also is excreted with an induced osmotic diuresis. Thus, multiple doses are required.

The addition of a hyperoncotic colloid, e.g. dextran, to the hypertonic saline results in a much more sustained plasma volume expansion and circulatory response. However, in clinical situations with relatively sustained circulatory leaks such as internal hemorrhaging or burn induced permeability increases, then even a hypertonic saline dextran solution is only transiently effective. Repeated infusions of hypertonic saline dextran can be given, but again they must be limited by the resultant hypernatremia or elevated sodium levels. Also, many physicians have concerns that colloid therapy is contraindicated in trauma and burns. Additionally, high serum levels of a colloid such as dextran can be associated with coagulation and blood typing disorders. Therefore an effective solution to treat hypodynamic shock would be safer as well as less expensive if colloids were not included.

Hypertonic resuscitation is particularly difficult in pediatric hypovolemia, because critically ill children often suffer from a combination of dehydration and hypovolemia. Thus, the pediatric patient frequently has a high serum sodium before any therapy is given and hypertonic saline may not be safely used. Therefore, a safer solution to treat these critically ill children with existing dehydration is needed.

Resuscitation with hypertonic solutions has also been used in several other hypodynamic circulatory states, such as during and after surgery, for burn injuries and after organ transplantation, where hypodynamic shock is threatened or experienced. A small bolus of a hypertonic solution delivered in the field could stabilize blood pressure and cardiac output long enough to allow transportation to a treatment center. Initial resuscitation in emergency rooms with small volumes of hypertonic saline rapidly and effectively stabilize cardiovascular function for diagnostic evalutation and prior to anesthesia and surgery. Unfortunately, current hypertonic solutions of sodium salts can only be used in one dose because of the resulting hypernatremia.

There thus exists a longfelt need for an effective hypertonic solution for treating shock victims without increasing serum sodium to excessive or dangerous levels. Administration of small volumes of such solutions should result in the rapid improvement of circulatory function. Multiple doses could be effectively given and safely tolerated. Additionally, the solution should be inexpensive and have a long shelf life. The present invention satisfies these needs and provides related advantages as well.

SUMMARY OF THE INVENTION

The invention provides a physiologically acceptable solution for treating hypodynamic circulatory shock in a mammal containing one or more reabsorbable solutes and a sodium salt and having an osmolarity in excess of about 1000 mOsms, preferably between 1000 and 3000 mOsms, most preferably about 2400 mOsms. The ratio of the reabsorbable solute to sodium salt is preferably between 1:1 and 1:3 osmolar parts. The reabsorbable solutes can be sugars, amino acids, derivatives or combinations thereof. The solution can be administered in a therapeutically effective dose to prevent and treat hypodynamic shock.

DETAILED DESCRIPTION OF THE PREFERRED EMBODIMENT

The present invention provides a physiologically acceptable solution which is hyperosmotic with respect to blood plasma and has utility in treating patients experiencing or threatening to experience hypodynamic shock. When given a small volume of the solution, on the order of 4 to 6 ml/kg of body weight, patients who have lost a significant proportion of their blood volume exhibit immediate and improved circulatory function as indicated by increased arterial pressure, cardiac output, and oxygen consumption and lowered peripheral resistance. In addition, blood flow to the kidneys and other vital organs may be augmented and urine output is unexpectedly and rapidly increased, thereby decreasing the possibility of acute renal failure, a major complication of shock. Most importantly, the present invention functions to resuscitate without a concomitant large increase in serum sodium. In addition, the solution is unexpectedly more effective after a second dose. Thus, multiple doses can effectively and safely be administered.

In one embodiment, the physiologically acceptable solution comprises a hyperosmotic concentration of a reabsorbable solute (in excess of about 1000 mOsms, preferably about 1,000 to 3000 mOsms). This physiologically acceptable solution is inexpensive to manufacture. As another aspect of the invention, the physiologically acceptable solution is easily administered by rapid bolus infusion of approximately 4 to 6 ml/kg of body weight and results in a rapid normalization of circulatory function. Multiple additional doses can be safely given as needed.

The present invention provides a physiologically acceptable solution which is hyperosmotic with respect to blood plasma and comprises a reabsorbable solute and a sodium salt. The term "physiologically acceptable" as used herein means that a small volume of the solution can be injected directly into a mammal without inducing pathological changes, such as an immune response or metabolic alterations due to toxicity. The physiologically acceptable solution has particular utility for use in preventing or treating hypodynamic shock, and results in an unexpected improvement in circulatory function especially in multiple doses which allow effectiveness for at least several hours. The solution is effective when administered in small quantities, permitting relatively easy transport and rapid administration, thereby facilitating easy and effective treatment at or near the site of injury.

The solution comprises sodium salts and reabsorbable solutes which are present in concentrations exceeding those of human blood plasma, thus establishing an osmotic gradient across the walls of the blood vessels. Preferably the hypertonic solution comprises about one osmolar part reabsorbable solutes and between one and three osmolar parts sodium salts.

As used herein, "reabsorbable solute" refers to a moiety less than about 1000 MW which can be substantially reabsorbed by the proximal tubules of the kidney. Alternatively, such solutes do not rapidly enter the cellular space and are not rapidly excreted. The reabsorbable solutes include but are not limited to simple sugars and their derivatives, amino acids and their derivatives, short chain peptides and acetoacetate. The best sustained osmotic expansion will occur with a mixture of several different sugars and amino acids, as different sugars and amino acids have different renal reabsorption carriers in the proximal tubule. Thus, infusion of a mixture of different solutes will result in less carrier saturation. Less carrier saturation limits the renal losses of solute and water and sustains volume expansion.

Preferably the sodium salt is sodium chloride or sodium acetate, although other anions such as bicarbonate, carbonate or lactate can also be used in place of or in combination with chloride.

The concentration of the reabsorbable solution is selected to provide an osmolarity which is sufficiently high so as to be effective in restoring circulatory function, without exerting detrimental effect on the cells and tissues or causing adverse physiological effects such as convulsions. Preferably, the osmolarity is between about 1000 to about 3000 mOsms, e.g., 2000 to 2800 mOsms, and ideally about 2400 mOsms. The hypertonic solution consists of between 1 and 3 osmolar parts sodium salts mixed with 1 osmolar part of reabsorbable solutes.

Different embodiments with different total osmolarity could have different clinical applications. For example, a solution with a total osmolality of 1000–1500 mOsms would be useful in the intensive care unit where fluids are normally continuously infused with the rate adjusted as needed to maintain blood volume, cardiac output, and oxygen delivery. A more concentrated solution of 2400–3000 mOsms would be a useful solution for paramedics to begin pre-hospital resuscitation with an intravenous or intraosseous bolus infusions of 2-10 ml/kg. These volumes are easily administered by civilian paramedics, through small bore catheters or intraosseous infusion needles. This solution would provide rapid volume expansion and the infusion could be repeated if needed without increasing the sodium as much as occurs with other hypertonic saline solutions. Finally, a substantially saturated solution would be useful, for example, for military corpsmen in that the effective dose could be greatly reduced to a volume the size of a single syringe. This concentration would allow more life-saving doses to be carried into the field.

A hyperosmotic solution is advantageously utilized to treat hypodynamic circulatory shock resulting from such cases as hemorrhage, trauma, burns, or sepsis. It is also useful to treat acute renal failure and cerebral edema. The solution is administered in the field or can be used as an initial treatment in an emergency room or critical care unit where a patient exhibits rapid blood loss or unresponsive hypodynamic circulation. The solution may be infused rapidly in a single bolus through a vascular catheter or may be injected directly into a peripheral vessel or into red bone marrow, saving critical time. The solution is effective in unexpectedly low dosages, about 4 to 6 ml/kg of body weight, which amounts to only about 1/10 to 1/80 the volume presently used to treat victims exhibiting shock through conventional volume replacement therapy. It is unexpectedly effective and safe in multiple doses. It effectively treats many forms of circulatory shock without causing fluid overload or other complications. Because only such small volumes are necessary, logistical problems of providing the solution at the site of injury are obviated. The same volume of fluid necessary to treat one patient through conventional therapy may be effectively used to treat many patients when a hyperosmotic solution is utilized. In addition, hypertonic resuscitation with the hypertonic solution is safer with existing dehydration and in critically ill children. The most effective solutions appear to contain a combination of saline, glucose and a mixture of amino acids. Treatment with saline/glucose alone results in exceedingly high urinary output due to high serum glucose and glucose excretion. Hypertonic saline with glucose or glucose alone can be infused without increasing sodium, but only a mixture of saline/glucose/amino acids can resuscitate well without increasing plasma sodium levels and without causing excessive urine losses.

After administration of a small volume of a hyperosmotic solution, various indicators of circulatory function are found to rapidly achieve normality and to sustain such normality. Among these indicators are arterial pressure, cardiac output, oxygen consumption, peripheral resistance, urine output, cellular membrane potentials and intracellular electrolyte balance. In addition to a single small volume infusion, multiple doses of solution in continuous infusions can be given in a safe and effective manner. This solution not only limits hypernatremia but ensures a lower risk of convulsions.

The hyperosmotic solution can be used alone or in conjunction with other treatments or solutions. For example, it can be desirable to add a colloid, such as dextran in an hyperoncotic concentration. See U.S. Pat. Nos. 4,927,806 and 4,908,350 which are incorporated herein by reference.

The following examples are intended to illustrate but not limit the invention.

The three solutions described above and in the examples are shown by osmolar parts and mg/ml. All three solutions are 2400 mOsms total osmolarity.

|  | HS | | HSG | | HSGAA | |
| --- | --- | --- | --- | --- | --- | --- |
|  | Osm, % | mg/ml | Osm, % | mg/ml | Osm, % | mg/ml |
| NaCl | 100 | 75 | 62 | 45 | 62 | 45 |
| Glucose | 0 | 0 | 38 | 173.2 | 13 | 58.9 |
| Amino Acids | 0 | 0 | 0 | 0 | 25 | 63.4 |

Osm = osmolar parts

EXAMPLE I

Treatment of Hypodynamic Circulatory Shock

Solutions of varying composition were used to treat hypodynamic circulatory shock in adult sheep weighing 40 to 50 kg. All solutions were made by dissolving the appropriate amounts of sodium salt, sugars or amino acids in deionized distilled water and stored at 4° C. until use. As used herein HS refers to hypertonic saline (100% NaCl, 2400 mOsms), HSG refers to NaCl plus glucose (2400 mOsms, total, 62% NaCl, 38% glucose), and HSGAA is NaCl, glucose and a mixture of amino acids (12.6 g Travasol (Baxter, Inc., Deerfield, Ill.)/200 ml HSG; 2400 mOsms, total, 62% NaCl, 13% glucose, 25% amino acids).

Chronic cannulation of the thoracic aorta, superior vena cava and pulmonary artery were performed on sheep anesthetized with halothane/nitrous oxide using neck vessels for access, and silastic and Swan-Ganz thermodilution catheters (Edwards Laboratories, Santa Ana, Calif.) inserted. A Foley catheter was emplaced to monitor urine output. Food and water were withheld for 24 to 36 hours before the beginning of the experimental protocol. Experiments were performed at least 72 hours after surgery.

All experiments were conducted on unanesthetized animals kept unrestrained in cages. Physiological parameters measured and recorded during experiments included vascular pressures (arterial, central venous, pulmonary artery and pulmonary wedge), cardiac output, urine flow rate, heart rate and respiratory rate. Blood samples were taken for subsequent analysis of hematocrit, serum osmolarity and serum $Na^+$, $K^+$ and $Cl^-$ and plasma protein. After an initial one hour period of baseline data collecting, the sheep were bled to a mean arterial pressure of 50 mm Hg, and maintained at 40 to 55 mm Hg by continued bleeding for the next two hours. This requires removal of 1.4 to 1.8 liters of blood. Measurement protocols followed those detailed in Example II.

Initially, a single sheep was subjected to three experiments. Each experiment was performed one week apart. After each hemorrhage, the sheep received an infusion with 200 ml, or about 4 ml/kg of either hypertonic sodium chloride, HS, (2400 mOsms), hypertonic sodium chloride and glucose, HSG, (2400 mOsms) or hypertonic sodium chloride, glucose, and amino acids, HSGAA, (2400 mOsms). One hour later, the animal was again infused with a second 200 ml infusion. As indicated in Table 3, the increase in plasma sodium is greater after HS as compared to HSG and HSGAA; however, cardiovascular output, urinary output (Table 1), and plasma volume expansion are nearly equal. With the infusion of any of the three solutions, the urinary output increased 2.5 to 3.5 fold over baseline during the first hour following infusion. There is yet another dramatic increase in urinary output after a second bolus infusion, especially with HSG. The HSG solution caused an elevated plasma glucose (Table 2) and an excessive urinary output or diuresis (Table 1). While some diuresis is beneficial, excessive diuresis limits the volume expansion and resuscitation effectiveness. The HSGAA solution was equally effective as HS in resuscitation and improvement in cardiac output; however, plasma sodium levels only slightly increased. Therefore, the hypertonic sodium chloride solution with both glucose and a mixture of amino acids can provide the benefits of hypertonic resuscitation to those critically ill patients who require larger volumes or those in which hypernatremia is contraindicated.

The following abbreviations apply to the tables below:
HS=Hypertonic Saline (2400 mOsms, 100% NaCl)
HSG=Hypertonic Saline/Glucose (2400 mOsms total, 62% NaCl, 38% glucose)
HSGAA=Hypertonic Saline/Glucose/Amino Acids (2400 mOsms total, 62% NaCl, 13% glucose, 25% mixed amino acids)

The results from experiments for sheep number 207 are shown below.

TABLE 1

| SHEEP 207 Urinary Output, ml/30 min | | | |
|---|---|---|---|
| | EXPERIMENT 2 HS | EXPERIMENT 2 HSG | EXPERIMENT 3 HSGAA |
| Baseline | 9 | 13 | 16 |
| End of Hemorrhage | 4 | 5 | 8 |
| 1st Bolus | 62 | 95 | 85 |
| 60 min. post 1st Bolus | 18 | 28 | 45 |
| 2nd Bolus | 157 | 240 | 168 |
| 60 min. post 2nd Bolus | 90 | 230 | 44 |

TABLE 2

| SHEEP 207 Plasma Glucose Concentration, mg/dl | | | |
|---|---|---|---|
| | HS | HSG | HSGAA |
| Baseline | 74 | 73 | 68 |
| End of Hemorrhage | 125 | 187 | 168 |
| 1st Bolus | 96 | 570 | 346 |
| 60 min. post 1st Bolus | 101 | 365 | 207 |
| 2nd Bolus | 91 | 597 | 328 |
| 60 min. post 2nd Bolus | 86 | 381 | 205 |

TABLE 3

| SHEEP 207 Plasma Sodium, mEq/L | | | |
|---|---|---|---|
| | HS | HSG | HSGAA |
| Baseline | 154 | 157 | 157 |
| End of Hemorrhage | 151 | 156 | 156 |
| 1st Bolus | 165 | 156 | 157 |
| 60 min. post 1st Bolus | 160 | 161 | 158 |
| 2nd Bolus | 176 | 164 | 165 |
| 60 min. post 2nd Bolus | 170 | 166 | 164 |

EXAMPLE II

Physiological Measurements

Vascular pressures were measured with a Gould P23 pressure transducer (Gould, Inc., Oxnard, Calif.) connected to a multichannel strip chart recorder for continuous monitoring. Transducers were leveled to the point of the shoulder. Cardiac output was measured by thermodilution, using a Model 9520A Cardiac Output Computer (Edwards Laboratories, Santa Ana, Calif.). Urine was collected in a closed drainage system equipped with a graduated cylinder. Hematocrits were determined with an IEC Microhematocrit Centrifuge (Damon Instruments, Needham Heights, Mass.). Sodium and potassium were measured by a Model 143 Flame Photometer (Instrumentation Laboratories, Lexington, Mass.). Osmolarity was determined on an Osmette A Freeze Point Osmometer (Precision Instruments, Sudbury, Mass.). Plasma volume was measured by the Evans Blue dye dilution technique (Gibson et al., J. Clin. Invest., 16:301 (1937) which is incorporated by reference) and also calculated from the drop in plasma protein after expansion.

EXAMPLE III

Treatment of Circulatory Shock with Hyperosmotic Solutions

Studies were performed to compare the efficacy of hypertonic sodium chloride (HS) with hypertonic sodium chloride plus glucose and amino acids (HSGAA). For the following example, a total of 7 sheep were studied and the data represent a mean value. As in Example I, the sheep were bled for two hours after an initial one hour period of baseline data were collected. A single bolus infusion of about 4 ml/kg of each solution was given to the sheep, who were monitored for an hour before a second bolus infusion was given. All solutions initially and effectively normalized blood pressure. The response of cardiac output to the bolus infusions was a slight increase over the baseline for both HS and HSGAA (Table 4). Over the ensuing one hour observation period, both of the solutions caused a decrease below baseline. After a second bolus infusion, cardiac output was 40%–65% greater than baseline for both solutions. HS alone resuscitated with higher serum sodium levels than HSGAA, as shown in Table 6. Both urinary output (Table 5) and plasma volume expansion (Table 7) are essentially equivalent for both solutions.

The overall resuscitation after treatment with the HSGAA solution was more effective than either with saline alone or saline plus glucose (see Example I). Additionally, only the HSGAA resuscitated well without a corresponding elevation in sodium levels or excessive urine losses.

The results for 7 sheep are shown. Abbreviations are those used in Example I. Data represent a mean value±standard deviation.

TABLE 4

| | Cardiac Output, L/min | |
|---|---|---|
| | HS | HSGAA |
| Baseline | 5.0 ± 0.2 | 5.1 ± 0.2 |
| End of Hemorrhage | 1.9 ± 0.2 | 2.3 ± 0.2 |
| 1st Bolus | 5.7 ± 0.4 | 5.8 ± 0.7 |
| 60 min. post 1st Bolus | 4.1 ± 0.3 | 3.6 ± 0.3 |
| 2nd Bolus | 6.7 ± 0.5 | 8.6 ± 0.6 |
| 60 min. post 2nd Bolus | 4.5 ± 0.2 | 4.4 ± 0.3 |

TABLE 5

| | Urine Output, ml/30 min | |
|---|---|---|
| | HS | HSGAA |
| Baseline | 14 ± 1.7 | 15 ± 1.8 |
| End of Hemorrhage | 5 ± 2 | 4 ± 0.9 |
| 30 min. post 1st Bolus | 81 ± 18 | 106 ± 23 |
| 60 min. post 1st Bolus | 46 ± 14 | 45 ± 15 |
| 30 min. post 2nd Bolus | 164 ± 29 | 172 ± 23 |
| 60 min. post 2nd Bolus | 89 ± 16 | 58 ± 12 |

TABLE 6

| | Plasma Sodium, mEg/L | |
|---|---|---|
| | HS | HSGAA |
| Baseline | 151 ± 2.4 | 150 ± 1.7 |
| End of Hemorrhage | 149 ± 1.4 | 151 ± 1.4 |
| 1st Bolus | 166 ± 1.4 | 154 ± 1.3 |
| 60 min. post 1st Bolus | 160 ± 1.3 | 154 ± 1.6 |

TABLE 6-continued

| | Plasma Sodium, mEg/L | |
|---|---|---|
| | HS | HSGAA |
| 2nd Bolus | 174 ± 1.8 | 159 ± 2.0 |
| 60 min. post 2nd Bolus | 167 ± 2.0 | 158 ± 1.8 |

TABLE 7

| | Plasma Volume, ml/kg | |
|---|---|---|
| | HS | HSGAA |
| Baseline | 45 | 45 |
| End of Hemorrhage | 30 | 30 |
| 1st Bolus | 43 | 43 |
| 60 min. post 1st Bolus | 37 | 35 |
| 2nd Bolus | 50 | 49 |
| 60 min. post 2nd Bolus | 42 | 42 |

NOTE: These values were calculated from mean changes in plasma protein.

Although the invention has been described with reference to the presently-preferred embodiment, it should be understood that various modifications can be made by those skilled in the art without departing from the invention. Accordingly, the invention is limited only by the following claims.

We claim:

1. A method of preventing or treating hypodynamic circulatory shock in a mammal, comprising the step of administering to said mammal in a condition or potentially in a condition of shock, a therapeutically effective dose of a physiologically acceptable solution, said solution comprising reabsorbable solutes and a sodium salt, said reabsorbable solutes consisting essentially of at least one sugar or a derivative of a sugar and at least one amino acid or a derivative of an amino acid and said solution having an osmolarity in excess of 1000 mOsms.

2. The method of claim 1, wherein said osmolarity of said solution is between 1000 to 3000 mOsms.

3. The method of claim 1 wherein said solution is substantially saturated with said reabsorbable solutes and said sodium salt in proportionate osmolar amounts.

4. The method of claim 1, wherein said osmolarity is approximately 2400 mOsms.

5. The method of claim 1, wherein said physiologically acceptable solution is infused intravascularly.

6. The method of claim 1, wherein said therapeutically effective dose is equal to or less than 4–6 ml/kg body weight.

7. The method of claim 1, wherein said reabsorbable solutes consists essentially of a mixture of several different sugars and amino acids.

* * * * *